United States Patent
Kaji

Patent Number: 5,964,224
Date of Patent: Oct. 12, 1999

[54] METHOD FOR TREATING AMYOTROPHIC LATERAL SCLEROSIS AND A THERAPEUTIC AGENT THEREFOR

[76] Inventor: Ryuji Kaji, 19-7, Sen-cho 2-chome, Ootsu-shi, Shiga-ken, 520-0863, Japan

[21] Appl. No.: 09/019,630

[22] Filed: Feb. 6, 1998

[30] Foreign Application Priority Data

Feb. 10, 1997 [JP] Japan .................................. 9-041604

[51] Int. Cl.⁶ .............................................. A61B 19/00
[52] U.S. Cl. ............................................ 128/898; 128/897
[58] Field of Search .................................... 128/897, 898; 514/52, 561; 536/26.44; 562/559

[56] References Cited

PUBLICATIONS

Lacomblez et al. "Dose–ranging study of riluzole in amyotrophic lateral sclerosis" *The Lancet 347*, 1425–431 (1996).
Cudkowicz et al. "Intrathecal administration of recombinant human superoxide . . . " *Neurology 49*, 215–222 (1997).
Doré et al. "Rediscovering an old friend, IGF–1: potential use in the treatment . . . " *TINS 20*, 326–331 (1997).
Friedlander et al. "Inhibition of ICE slows ALS in mice" *Nature 388*, 31 (1997).
Gourie–Devi et al. "Temporary amelioration of symptoms with intravenous . . . " *J. Neur. Sci. 150*, 167–172 (1997).
Gredal et al. "A clinical trial of dextromethorphan in amyotrophic lateral sclerosis" *Acta Neurol Scand 96*, 8–13 (1997).
Kostic et al. "Bcl–13 2: Prolonging Life in a Transgenic Mouse Model of Familial . . . " *Science 277*, 559–562 (*1997).
Penn et al. "Intrathecal Ciliary Neurotrophic Factor Delivery for Treatment . . . " *Neurosurgery 40*, 94–199 (1997).
Reider et al. "Lou Gehrig and Amyotrophic Lateral Sclerosis" *Arch Neurol 54*, 527–528 (1997).
Mizisin et al. "Toxic neuropathies" *Current Opn. Neurology 8*, 367–371 (1995).
Pfohl–Leszkowicz et al. "Effects of Cobalmin Derivatives on in Vitro Enzymatic DNA . . . " *Biochem. 30*, 8045–8051 (1991).
Akaike et al. "Protective effects of a vitamin $B_{12}$ analog, methylcobalamin . . . " *E. J. Pharm. 241*, 1–6 (1993).
Watanabe et al. "Ultra–high dose methylcobalamin promotes nerve regeneration . . . " *J. Neurol. Sci. 122*, 140–143 (1994).
Kelley et al. "Use of Electrophysiologic Tests to Measure Disease Progression . . . " *Muscle & Nerve 13*, 471–479 (1990).
Kimura "Electrodiagnosis in Diseases of Nerve and Muscle: Principles and Practice", Edition 2, 83–89 (1989).

*Primary Examiner*—Mickey Yu
*Assistant Examiner*—Dinh X. Nguyen
*Attorney, Agent, or Firm*—Heslin & Rothenberg, P.C.

[57] ABSTRACT

A method for treating amyotrophic lateral sclerosis (ALS) and a therapeutic agent therefor are provided. The therapeutic agent comprising ultra-high doses of methylcobalamin (for example, from about 15 mg to about 500 mg per day) is administered to a patient with ALS intramuscularly, subcutaneously or intravenously for from about a week to about 2 years to ameliorate or improve both the clinical symptoms and an objective clinical measure in ALS or retard the muscle weakness caused by ALS.

9 Claims, 1 Drawing Sheet

METHOD FOR TREATING AMYOTROPHIC LATERAL SCLEROSIS AND A THERAPEUTIC AGENT THEREFOR

FIELD OF THE INVENTION

The present invention relates to a method for treating amyotrophic lateral sclerosis (ALS) and a therapeutic agent therefor.

BACKGROUND OF THE INVENTION

ALS is a progressive disease affecting upper and lower motor neurons in the brain and the spinal cord, culminating in a death usually within 2–3 years after the onset of the symptoms.

Patients with ALS have no cure or treatment effective in improving clinical signs or parameters, although riluzole has been reported to prolong life without tracheostomy by 1–3 months in a subgroup of ALS. Other agents such as dextromethorphan, superoxide dismutase, vitamin E, ciliary neurotrophic factor have not yet convincingly shown their potency in improving the clinical symptoms or prolonging life in patients with ALS. Anecdotal or preliminary observations have also been made on the beneficial effects of cyclophosphamide and IGF-1 (insulin-like growth factor-1).

ALS patients generally show reduced amplitudes of muscle potentials after peripheral nerve stimulation (compound muscle action potentials or CMAPs). CMAPs can therefore be used as an objective measure of muscle power, and their decrease is related to the development of muscle weakness.

SUMMARY OF THE INVENTION

It is an object of the present invention to provide a safe, simple and effective method and therapeutic agent for ameliorating or improving the clinical signs and symptoms of ALS in humans.

The present invention relates to a method for treating patients with ALS by means of intramuscular, subcutaneous or intravenous administration of a therapeutic agent comprising an ultra-high dose of methylcobalamin. Using low-dose methylcobalamin as a control, I have found that 15–500 mg/day, preferably 15–100 mg/day, of methylcobalamin (i.m., s.c. or i.v. for 14 days) significantly increases the parameter of muscle power (compound muscle action potentials or CMAPs) and improves the subjective weakness in patients with ALS.

In another aspect, the invention relates to a unit dosage form, which comprises methylcobalamin in an amount of from about 15 mg to about 500 mg, preferably from about 15 mg to 200 mg, or more preferably from about 15 mg to about 100 mg in powder or in about 1 mL to about 40 mL of a pharmaceutically acceptable solvent such as ethanol, normal saline and a buffer solution in a vial or ampule. The therapeutic agent may comprise pharmaceutically acceptable preservatives and other therapeutically useful agents.

DETAILED DESCRIPTION OF THE INVENTION

Figure 1:
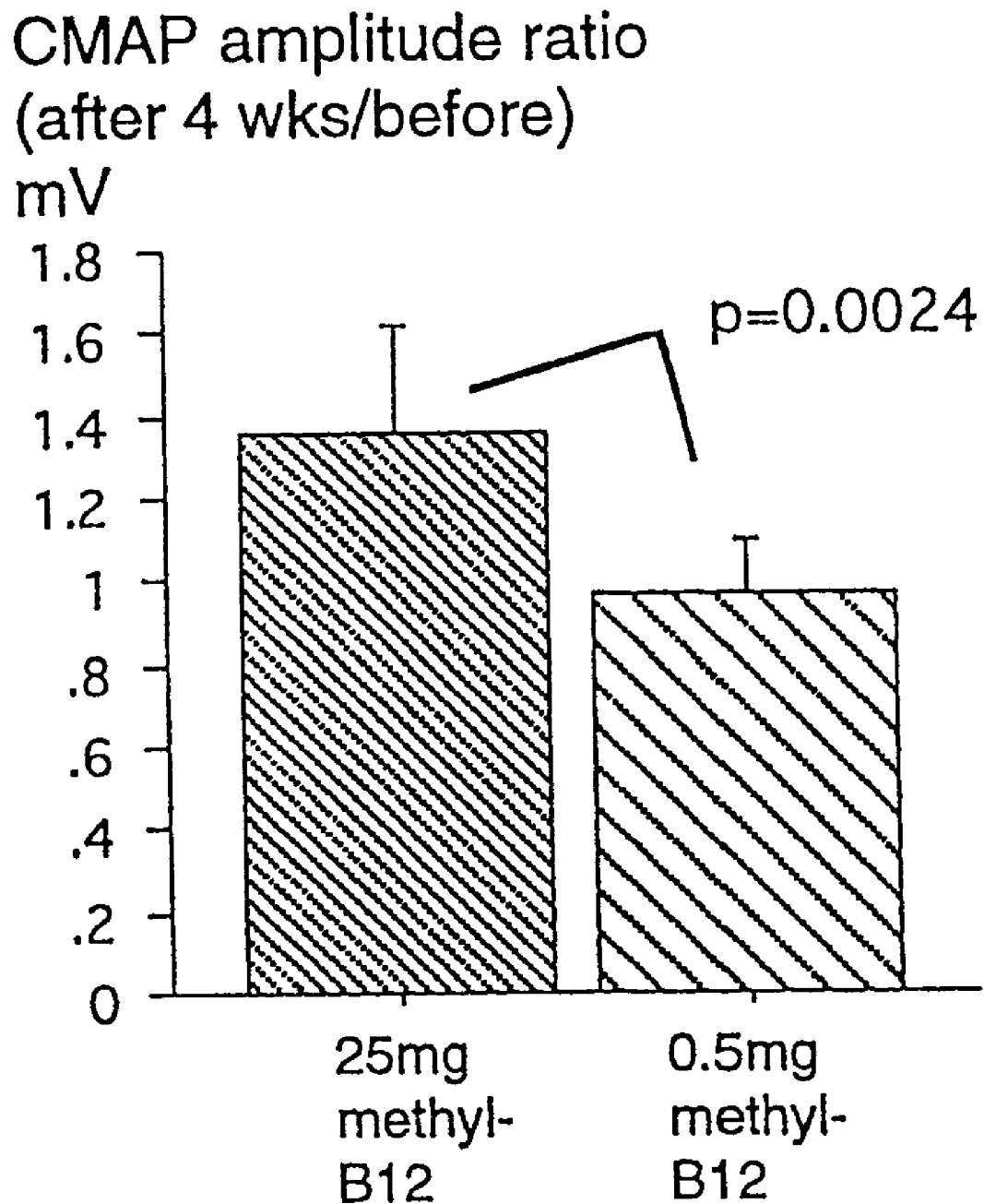
FIG. 1 is a bar graph showing the CMAP amplitude ratio for two groups of patients, a first group treated with 25 mg/day of methylcobalamin and a second group treated with 0.5 mg/day of methylcobalamin.

The therapeutic agent of the present invention comprises an ultra-high dose of methylcobalamin. As a unit dosage form, the agent is provided as about 15 mg to about 500 mg methylcobalamin and 1 mL to 40 mL of a pharmaceutically acceptable solvent in a vial or ampule. Preferably the unit dosage form contains from about 15 mg to about 100 mg of methylcobalamin and 1 to 10 mL of a pharmaceutically acceptable solvent in a dark-colored vial or ampule. Pharmaceutically acceptable solvents include ethanol, sterile normal saline and a sterile buffer solution of pH about 5 to about 8.

Methylcobalamin is a vitamin B12 analog in which the cyanate residue of vitamin B12 (cyanocobalamin) is replaced by methyl residue. Its chemical formula is $C_{63}H_{91}CoN_{13}O_{14}P$, and its molecular weight is 1344.4. Methylcobalamin may be obtained by reducing and methylating cyanocobalamin, but it is also commercially available as a red powder in a 0.5 mg ampule, from Eisai Co. Ltd (Japan).

According to the present invention, a therapeutic agent used for treating ALS patients comprises from about 15 mg to about 500 mg, preferably from about 15 mg to 200 mg, or more preferably from about 15 mg to 100 mg of methylcobalamin dissolved or suspended in from about 1 mL to about 40 mL of a pharmaceutically acceptable solvent in a vial or ampule. The term of "a pharmaceutically acceptable solvent" means any solvent which is used as a proper medium for an intramuscular, subcutaneous or intravenous injection. Such a solvent includes, for example, ethanol, sterile normal saline and sterile buffer solutions such as phosphate buffer, acetate/sodium acetate buffer, Tris-HCl buffer and other buffer solutions in which methylcobalamin is stable, with pH adjusted to from about 5 to about 8.

Alternatively, from about 15 mg to about 500 mg, preferably from about 15 mg to about 200 mg, or more preferably from about 15 mg to about 100 mg of the powder of methylcobalamin can be contained in a dark-colored vial or ampule, so that a solution or suspension can be made immediately before use with from about 1 mL to about 40 mL of a pharmaceutically acceptable solvent such as ethanol, sterile normal saline and a sterile buffer solution. The buffer solutions suitable for this purpose include those described above.

Methylcobalamin is light-sensitive, and is easily degraded into hydoxycobalamin. Therefore it is essential to store the agent in a dark place. It is not heat-labile nor sensitive to humidity.

D-Mannitol and other pharmaceutically accepted preservatives may be used as a preservative in the therapeutic agent of the present invention.

From about 15 mg to about 500 mg (from about 0.3 mg/kg to 10 mg/kg body weight), preferably from about 15 mg to about 200 mg (from about 0.3 mg/kg to 4 mg/kg), or more preferably from about 15 mg to about 100 mg (from about 0.3 mg/kg to 2 mg/kg) per day of methylcobalamin is given intramuscularly, subcutaneously or intravenously to patients with ALS for from about 1 week to about 2 years, depending on their clinical symptoms.

The intramuscular route is preferable to the intravenous route, because it provides a longer half life in the blood level.

In case of administering the dose of more than 100 mg/day, care must be taken to avoid the adverse reaction which might occur. When i.v. drip infusion is employed, care must be taken to avoid light by covering the infusion bottle.

Methylcobalamin in 0.5 mg ampules has been on the market for clinical uses in peripheral neuropathies in Japan. Its safety has been assessed by Eisai Co Ltd, Japan in animal models as follows.

Subacute toxicity assessment in rats, in doses of 0.5, 5.0, and 20.0 mg/kg/day given intraperitoneally for 30 days, revealed no significant changes in the general conditions, body weight, blood and urine chemistry, organ weights and histological findings. It was also examined in beagles using 0.5. 5.0 and 50.0 mg/kg/day given intravenously for 90 days, again with normal findings. The histological finding of increased eosinophilic granules in the proximal tubules in the kidney was however noted in a dog given 50.0 mg/kg/day. No changes were noted in the epidydimis of this dog.

Chronic toxicity was screened in the rat, using the same doses as above but given for 6 months. No significant changes were found in the same studies as above. Beagles were also given the same regimen as above for long-term administration (6 months). Only dogs given 50.0 mg/kg/day showed increased eosinophilic granules in the proximal tubules in the kidney detected by light microscopy and increase in lysosomes by electron microscopy, lysosomal increase in the mesangeal cells in the renal glomeruli and the increased number of Kuppfer cells in the liver.

A study on the reproductive system was performed in embryos of the rat and the mouse during the period of organogenesis by giving 20 mg/kg/day intraperitoneally, or by using 50 mg/kg intravenously in the rat during the pre-gestation and postgestation period, the early pregnancy and organogenesis, and the perinatal and postnatal period. Another study was done in the rabbit during the organogenesis in the dose of 50 mg/kg/day. All these studies revealed no significant changes in the embryo, the fetus or the neonate of d these animals.

On rare occasions, animals given 50 mg/kg/day develop transient edema and redness of the skin, but no major side effects have been observed. Red urine may be found, but it soon disappears after discontinuing the administration.

Clinical Trials

To develop a symptomatic treatment for amyotrophic lateral sclerosis, I have compared the effects of ultra-high dose and low dose (25 mg/day and 0.5 mg/day, i.m. for 14 days) of methylcobalamin on the averaged compound muscle action potential amplitudes, which serve as an index of muscle power, in a double-blind trial.

CHAPs were recorded bilaterally from the abductor pollicis brevis, abductor digiti minimi and abductor hallucis muscles after stimulation of the median, ulnar and tibial nerves at the wrist or at the ankle. Amplitudes were measured from the baseline to the negative peak. In each patient, the average amplitude from the six muscles (averaged CMAPs) served as an index of the number of muscle fibers innervated by spinal motoneurons. The method employed was that of Kelly et al.[*Muscle Nerve* 10, 471–179 (1990)] and Kimura [in *Electrodiagnosis in diseases of nerve and muscle: principles and practice,* 2nd edition, F. A. Davis ed.(1989), pages 85–87], the disclosures of which are incorporated herein by reference.

No significant changes in CMAP amplitude have been found in 10 patients who had the low dose treatment either at 2 or 4 weeks after the start. By contrast, 12 patients assigned for ultra-high dose have demonstrated a significant increase at 4 weeks. No major side effects were seen. The method of the present invention provides a clinically useful measure to ameliorate or improve the clinical symptoms of ALS or retard the muscle weakness caused by ALS.

According to the present invention, an effective amount of the therapeutic agent of the present invention is intramuscularly, subcutaneously or intravenously administered to a patient with ALS once a day or separately at a clinically acceptable interval for from about 1 week to about 2 years to ameliorate or improve the clinical signs or symptoms of ALS or retard the muscle weakness caused by ALS.

The following examples are for illustrative purposes only and are in no way intended to limit the invention. It will be apparent to those of skill in the art that other embodiments are practicable and even intended.

EXAMPLE 1

(Double-blinded study)

Subjects and Methods

A total of 24 ALS patients without respiratory failure entered the study after giving an informed consent for the protocol approved by the Institutional Review Board. Twelve of them (High Dose Group; age 45–66 years, 5 men) received the ultra-high dose (25 mg/day or 360–610 $\mu$g/kg/day, i.m.) methylcobalamin and the other 12 (Low Dose Group; age 41–66 years, 6 men) received the low dose (0.5 mg/day or 7–13 $\mu$gAg/day, i.m.) as a control. The two groups were matched for age, disease durations (19.6±4.1 versus 21.7±3.2 months) and initial averaged CHAP amplitudes (5.27±0.84 versus 4.48±0.91 mV). The patients were blinded as to the dose. The examiner, who was not informed of the dose, measured CMAPs immediately before starting methylcobalamin (day 1), at the end of 2 weeks of administration (day 14) and at 4 weeks after the start (day 28).

Results

The Low Dose Group showed no significant changes in CMAP amplitude after treatment either at 2 or 4 weeks (p=0.60, repeated measures ANOVA). By contrast, the High Dose Group demonstrated a significant increase at 4 weeks (day 28, p=0.017, repeated measures ANOVA; p=0.038, paired t), but not at 2 weeks (day 14, p=0.46, paired t). The amplitude ratio between day zero and day 28 was used to compare the effects of treatment between groups; High Dose Group had a significantly higher ratio than Low Dose Group (p=0.030, unpaired t). Two patients in High Dose Group noted an improvement in gait and weakness. These clinical benefits and improved CMAPs usually lasted for 1–3 months, then followed by deterioration. Adverse reactions in High Dose Group included skin rash in one patient and mild elevation of serum GOT and GPT in another, both lasting for about a week. Serial changes of averaged CMAP amplitudes in low dose (0.5 mg/day i.m., n=12) group and high dose (25 mg/day i.m., n=12) group were examined. Methylcobalamin was given during day 0 through day 13. Comparison of the ratio of averaged CMAP amplitude at day 14 or at day 28 to that at day 0 in 2 groups showed that only the high dose group showed a significant increase in the ratio at day 28. The time course of averaged CMAP amplitude changes in a patient with ALS who was given 50 mg/day of methylcobalamin during day 0 day through 13 was examined. There was an abrupt increase of the amplitude during and after the treatment.

This double blind study documented an increase of averaged CMAP amplitudes at day 28 in the High Dose Group, which suggests either nerve terminal sprouting or increased efficacy of neuromuscular transmission. The latency to the improvement is possibly due to the time required for the soma of the motoneuron to upregulate DNA transcription for nerve sprouting and transmitter production. The averaged CMAP tend to be more affected by the tibial nerves than the other nerves in the upper limbs, because the tibial CMAP amplitude is almost twice as large as the others in normal subjects. This however is suited for representing both upper and lower limbs equally, since two nerves are included for the former, only one for the latter.

CMAP amplitudes were averaged in 10 patients with ALS treated with a low dose of methycobalamin (0.5 mg/day i.v. for 2 weeks). Those before the treatment and those 2 weeks after the completion of the treatment were compared. No significant changes were found.

CMAP amplitudes were averaged in 12 patients with ALS treated with a high dose of methylcobalamin (15 mg/day i.v. for 2 weeks). Those before the treatment, those at the end of the treatment and those 2 weeks after the completion of the treatment were compared. Although there was a tendency toward increase of CMAPs at 2 weeks after the completion of the treatment, no statistically significant differences were found.

CMAP amplitudes were averaged in 12 patients with ALS treated with an ultra-high dose of methylcobalamin (25 mg/day i.m. for 2 weeks). Those before the treatment, those at the end of the treatment and those 2 weeks after the completion of the treatment were compared. There was a statistically significant increase of CMAPs at 2 weeks after the completion of the treatment ($p<0.05$ ANOVA).

The ratio of averaged CMAP amplitudes at 2 weeks after the completion of the treatment (after 4 wks) was compared with those before the treatment. There was a statistically significant difference between the ratio of the ultra-high dose (25 mg/day i.m. for 2 weeks) group and that of the low dose (0.5 mg/day i.v. for 2 weeks) group ($P<0.05$; unpaired t-test). The differences are shown in FIG. 1.

The CMAP increase reflects improvement in clinical muscle wasting or weakness. Ultra-high dose methylcobalamin is the first therapy associated with improvement of both clinical symptoms and an objective clinical measure in ALS patients.

What is claimed is:

1. A method for treating amyotrophic lateral sclerosis (ALS) comprising parenterally administering to a patient in need of such treatment from about 15 mg to about 500 mg per day of methylcobalamin.

2. A method according to claim 1 wherein from about 15 mg to about 100 mg per day of methylcobalamin is administered.

3. A method according to claim 1 wherein from about 15 mg to about 500 mg per day of methylcobalamin is administered intramuscularly.

4. A method according to claim 1 wherein from about 15 mg to about 100 mg per day of methylcobalamin is administered intramuscularly.

5. A method according to claim 1 wherein from about 15 mg to about 500 mg per day of methylcobalamin is administered subcutaneously.

6. A method according to claim 1 wherein from about 15 mg to about 100 mg per day of methylcobalamin is administered subcutaneously.

7. A method according to claim 1 wherein from about 15 mg to about 500 mg per day of methylcobalamin is administered intravenously.

8. A method according to claim 1 wherein from about 15 mg to about 100 mg per day of methylcobalamin is administered intravenously.

9. A method according to claim 1 wherein said methylcobalamin is administered for a period of one week to two years.

* * * * *